(12) United States Patent
Giuliani et al.

(10) Patent No.: US 9,351,918 B2
(45) Date of Patent: May 31, 2016

(54) POLYGLYCEROL-AZELAIC ACID POLYESTERS FOR COSMETIC APPLICATIONS

(71) Applicant: GIULIANI S.P.A., Milan (IT)

(72) Inventors: Giammaria Giuliani, Milan (IT); Anna Benedusi, Milan (IT); Antonio Mascolo, Milan (IT); Barbara Marzani, Carbonara Al Ticino (IT); Guido Bregaglio, Gubbio (IT)

(73) Assignee: GIULIANI S.P.A., Milan (IT)

( * ) Notice: Subject to any disclaimer, the term of this patent is extended or adjusted under 35 U.S.C. 154(b) by 0 days.

(21) Appl. No.: 14/419,091

(22) PCT Filed: Aug. 2, 2013

(86) PCT No.: PCT/EP2013/066295
§ 371 (c)(1),
(2) Date: Feb. 2, 2015

(87) PCT Pub. No.: WO2014/020158
PCT Pub. Date: Feb. 6, 2014

(65) Prior Publication Data
US 2015/0196480 A1    Jul. 16, 2015

(30) Foreign Application Priority Data

Aug. 3, 2012    (IT) .......................... MI2012A001380

(51) Int. Cl.
*A61K 8/85*    (2006.01)
*A61K 8/86*    (2006.01)
*A61K 8/39*    (2006.01)
(Continued)

(52) U.S. Cl.
CPC . *A61K 8/86* (2013.01); *A61K 8/362* (2013.01); *A61K 8/39* (2013.01); *A61K 8/466* (2013.01); *A61K 8/85* (2013.01); *A61Q 5/00* (2013.01); *A61Q 5/02* (2013.01); *A61Q 5/12* (2013.01); *A61Q 17/00* (2013.01); *A61Q 17/005* (2013.01); *A61Q 19/00* (2013.01); *C08G 63/12* (2013.01); *C08G 63/668* (2013.01); *A61K 2800/54* (2013.01)

(58) Field of Classification Search
CPC ..... A61K 2800/54; A61K 8/362; A61K 8/39; A61K 8/85; C08G 63/12; C08G 63/668
See application file for complete search history.

(56) References Cited

U.S. PATENT DOCUMENTS 1,779,367 A    10/1930    Bruson
2008/0152607 A1    6/2008    Malle et al.

FOREIGN PATENT DOCUMENTS

GB    348593    5/1931
WO    2012007754    1/2012

OTHER PUBLICATIONS

International Search Report dated Nov. 28, 2013 corresponding to International Patent Application No. PCT/EP2013/066295; 4pages.
(Continued)

*Primary Examiner* — Rachael E Bredefeld
(74) *Attorney, Agent, or Firm* — Ohlandt Greeley Ruggiero & Perle L.L.P.

(57) ABSTRACT

A polyglycerol-azelaic acid polyesters and cosmetic compositions that incorporate them as active components in combination with a cosmetically acceptable vehicle. A process for producing esters and polyesters between azelaic acid and glycerol or oligomers thereof containing up to 10 monomer units.

19 Claims, 5 Drawing Sheets

(51) Int. Cl.
*A61K 8/362* (2006.01)
*C08G 63/668* (2006.01)
*C08G 63/12* (2006.01)
*A61Q 5/00* (2006.01)
*A61Q 5/02* (2006.01)
*A61Q 5/12* (2006.01)
*A61Q 17/00* (2006.01)
*A61Q 19/00* (2006.01)
*A61K 8/46* (2006.01)

(56) References Cited

OTHER PUBLICATIONS

Written Opinion dated Nov. 28, 2013 corresponding to International Patent Application No. PCT/EP2013/066295; 6 pages.
International Preliminary Report on Patentability dated Nov. 28, 2013 corresponding to Internation Patent Application No. PCT/EP2013/066295; 6pages.

POLYGLYCEROL-AZELAIC ACID POLYESTERS FOR COSMETIC APPLICATIONS

BACKGROUND

1. Field of the Disclosure

The present disclosure relates to polyglycerol-azelaic acid polyesters and their applications in the field of cosmetics.

2. Discussion of the Background Art

Azelaic acid is dicarboxylic acid with the IUPAC name nonanedioic acid and the structural formula (I) shown below:

(I)

This acid can be produced from oleic acid (cis-9-octadecenoic acid), a monounsaturated fatty acid, by ozonolysis followed by oxidative cleavage; during the reaction they form an azelaic acid molecule and a nonanedioic acid molecule.

Azelaic acid has been proven to be particularly effective in the topical treatment of comedonal acne and inflammatory acne (papulopustular, nodular and nodulocystic). Its use was developed from the observation that species of the *Pityrosporum ovale* (*Malassezia furfur*) genus are able to oxidise the unsaturated fatty acids present in sebum to dicarboxylic acids which competitively inhibit the tyrosinase enzyme. Due to its inhibitory effect against tyrosinase, the compound has also been used to treat melasma, lentigo maligna, hyperpigmentation and other diseases characterised by the abnormal proliferation of melanocytes.

Azelaic acid is also proven to be effective in treating hypermelanosis caused by physical and photochemical agents, with no evident lightening action on normal skin and without being photosensitising.

This acid has also shown a selective antiproliferative and cytotoxic effect on human malignant melanocytes (as is discussed in the article "Azelaic acid. A review of its pharmacological properties and therapeutic efficacy in acne and hyperpigmentary skin disorders", Fitton A., Goa K. L. Drugs 1991 May; 41 (5):780-98). The mechanism of this action is still unclear although it may be related to the ability of azelaic acid to inhibit mitochondrial oxidoreductase activity and DNA synthesis.

A problem related to the use of azelaic acid in topical formulations is that this acid, like other short-chain dicarboxylic acids, has an irritant effect when in contact with the skin; this side effect, which is generally temporary, may manifest itself as itching or tingling. The information contained in the literature indicates that the irritation potential of these substances decreases with increasing alkyl chain length, although longer chains do not retain the positive primary effects of azelaic acid illustrated above.

There is therefore a need for compositions which are able to deliver azelaic acid, whilst substantially reducing or eliminating the side effects.

SUMMARY

One of the purposes of this disclosure is to provide polymers or mixtures of compounds containing azelaic acid wherein this compound maintains its action, considerably reducing the occurrence of unwanted side effects which are typical of azelaic acid.

Other purposes of the disclosure are to provide a process for producing said mixtures, and to provide cosmetic compositions containing them.

These purposes are fulfilled, in accordance with the first aspect of the disclosure, by providing a linear or branched polyglycerol-azelaic acid polyester.

In accordance with certain aspects the polyglycerol-azelaic acid polyester of the disclosure is obtainable by reacting or condensing azelaic acid with polyglycerols with a polymerisation degree in the range from 1.5 to 10.

In accordance with another aspect, the present disclosure provides a method for producing mixtures of esters and polyesters obtained by condensing or reacting azelaic acid with a polyol selected from glycerol and oligomers thereof containing up to 10 units glycerol.

DETAILED DESCRIPTION OF THE PREFERRED EMBODIMENT

In accordance with a first aspect of the disclosure a polyglycerol-azelaic acid polyester is provided consisting essentially of at least one unit of azelaic acid and at least one unit of polyglycerol having a polymerisation degree from 1.5 to 10.

In certain embodiments the polyglycerol-azelaic acid polyester of the disclosure contains 1-20 units, preferably 2-10 units of polyglycerol.

In certain embodiments the polyglycerol has 3 units of glycerol and is polyglicerol-3.

Typically, the polyglycerol-azelaic acid polyester of the present disclosure does not contain mono or di-carboxylic acids other than azelaic acid.

The main component of esters and polyesters in this disclosure is glycerol and oligomers thereof. Glycerol is a tri-functional molecule and can therefore condense with other glycerol molecules to form dimers, trimers, oligomers and polymers. The simplest example is diglycerol or diglycerine which is obtained by condensing two glycerol molecules. The dehydration reaction may affect all three of the molecule's hydroxyl groups and therefore may have varying types of condensations: alpha-alpha (α-α, i.e. between two hydroxyl groups bonded to primary carbon atoms of two glycerol molecules); beta-beta (β-β, i.e. between two hydroxyl groups bonded to secondary carbon atoms of two glycerol molecules); and alfa-beta (α-β, i.e. between one hydroxyl group bonded to a primary carbon atom of a glycerol molecule and one hydroxyl group bonded to a secondary carbon atom of another glycerol molecule), as in the structures described below:

The number of possible isomers increases along with an increase in the polymerisation degree, for example, going from three different linear isomers for a diglycerol to eight different linear isomers for a triglycerol.

Intra-molecular reactions can also lead to the formation of cyclic products. Typically, the processes currently available for obtaining high purity polyglycerols can be divided into two types:
- methods aimed at removing cyclic products and other by-products, for example, as described in U.S. Pat. No. 3,968,169, the contents of which are fully incorporated here as a reference,
- methods for obtaining high purity linear products, for example, as described in U.S. Pat. No. 6,620,904, the contents of which are fully incorporated here as a reference,

For the purposes of this disclosure, glycerol and oligomers thereof containing up to 10 units of the monomer (polyglycerol-10), for example from 2 to 10 units of glycerol, have proven particularly suitable. In fact, an increase in the degree of polymerisation of polyglycerols corresponds to a decrease in the purity of the same, together with the presence of an increasingly higher number of fractions with different molecular weights, which renders the chemical and physical properties of the final polyesters less homogeneous. It should also be considered that as the degree of polymerisation, and therefore the molecular weight, increases, there is an increase in viscosity and a decrease in the hygroscopicity of the molecule. Finally, polyglycerols of up to 10 monomer units are commercially available, for example from Solvay, Spiga North Carasco (Genoa), Lonza (Basel), avoiding the necessity to synthesise this component.

Typically, polyglycerols can be synthesised using methods which allow the condensation of glycerol with alkaline catalysts (its dehydration) with the elimination of water. The result of this synthesis is normally a mixture of oligomers which can include unreacted glycerol, cyclic products and high oligomer products. Temperature, typically above 200° C., synthesis and vacuum duration conditions, promote the formation of the desired structures. Dehydration of glycerol achieves various polymers where glycerine molecules are linked by a "bridge" of oxygen. From glycerol, which contains three hydroxyl groups, the number of —OH increases by one for every glycerin molecule which is condensed, therefore diglycerol has four free —OH, triglycerol has five —OH, tetraglycerol six, and so on.

In the production of the polyesters in this disclosure, glycerol and oligomers thereof may be used in pure form, or a mixture thereof may be used.

In some forms of preparing the disclosure, glycerol or its oligomer in pure form was used.

In some embodiments of preparing the disclosure, polyglycerol-3 was used, typically the trimer wherein the three glycerol units are linked in α-α configuration:

The second component of esters and polyesters in this disclosure is azelaic acid. The synthesis of polyesters in this disclosure is carried out through the reaction of the first component (glycerol, its oligomers or mixtures thereof) and said acid.

Typically, the esterification reaction can be catalysed by acid or base. In some forms of preparing the disclosure an acid catalyst is used, for example para-toluenesulfonic acid, or no catalyst is added, in this case using the acidity of the azelaic acid itself.

Laboratory synthesis can be performed using various equipment. For example, it is possible to use a glass spherical reactor (flask) placed inside a microwave oven, equipped with an anchor stirrer, thermometer, dip tube for nitrogen, a Claisen distillation flask with a Graham condenser and finally an addition funnel. Alternatively, it is possible to use a reactor consisting of a 250 ml 2-neck pyrex glass flask, positioned inside an electric laboratory oven, and connected to a three-necked glass candlestick, which allows the metal rod to pass through for mechanical stirring of the product (central rod) and circulation of a flow of nitrogen. Reaction temperatures are variable and can range from around 145° C. to 180° C. in the case of microwave oven synthesis, and from around 130° C. to 220° C. in the case of electric oven synthesis.

Equimolar amounts of glycerol or oligomers thereof and azelaic acid are typically used for synthesis, or a slight excess of glycerol and oligomers thereof, for example of 5-10%, is introduced.

Typically, linear molecules are also present in the reaction environment, arising from the reaction between a secondary alcohol group and an acid group, as well as branched molecules.

By appropriately adjusting the molar ratios between reagents and the reaction times, a prevalence of the desired polyesters can be achieved in the reaction product.

The reaction between a diacid and a polyalcohol can lead to various products, from "simple" esters, resulting from the reaction of a diacid molecule and a polyglycerol molecule, to oligomers and polymers resulting from successive condensations of molecules containing acid groups and molecules with hydroxyl groups. As polyglycerol is a multifunctional reagent, you can also achieve the formation of cross-linked molecules (wherein various chains react with each other forming "bridges", producing insoluble products) or branched molecules. In the event that no crosslinking or branching occurs and polyesters are therefore linear, with G indicating a unit of glycerol or polyglycerol and AZ a unit of azelaic acid, the esters and polyesters in this disclosure can be represented schematically as $(-G-AZ-)_n$. The product obtained from the condensation reaction is a relatively complex mixture of esters and polyesters (-G-AZ-)$_n$ wherein the structure of the unit G and index n are both variables.

A second aspect of the disclosure relates to esters and polyesters obtained by the synthesis process described above.

In certain embodiments a polyglycerol-azelaic acid polyester consisting essentially of at least one unit of azelaic acid and at least one unit of polyglycerol having a polymerisation degree from 1.5 to 10 is provided obtained by condensing azelaic acid or cyclic anhydride of azelaic acid with polyglycerol having a polymerisation degree in the range from 1.5 to 10. Typically, the disclosure product comprises esters and/or polyesters derived from the condensation of glycerol or its oligomers up to polyglycerol-10, for example from 2 to 10 units, with structures containing an alternating residue of azelaic acid and one of glycerol or polyglycerol.

In accordance with some embodiments, the disclosure relates to polyglycerol-azelaic acid esters and/or polyesters obtained by condensing azelaic acid with the glycerol trimer wherein the three glycerol units are connected with α-α bonds, represented schematically below:

where index n is variable from 1 and 7

Typically, characterisation of the polyglycerol-azelaic acid esters and/or polyesters obtained can be done by chromatography, in particular using the SEC (Size Exclusion Chromatography) technique. This technique produces chromatograms which report peaks, corresponding to the output of a substance or fraction from the instrument in relation to time. This is achieved after calibrating the instrument with reference compounds, which have a hydrodynamic volume similar to those of the molecules or polymers being observed. For example, for a polystyrene of known molecular weight, the technique provides, among others, the following values:

Mn, number average molecular weight (average weight);
Mw, weight average molecular weight (weighted average);
D (polydispersity), ratio of Mw/Mn.

The closer the value of D is to 1, the greater the purity of the molecule.

In accordance with certain embodiments a polyglycerol-azelaic acid polyester is provided obtainable by reacting polyglycerol having from 2 to 10 glycerol units with azelaic acid or cyclic anhydride of azelaic acid specifically in a molar ration from 1:2 to 2:1.

In certain embodiments the polyglycerol-azelaic acid polyester contains at least one unit of azelaic acid and at least one unit of polyglycerol having a polymerisation degree of about 2.

Within the terms of the present application, the polymerisation degree is specifically referred to the oligomers of polyglycerol, and designs the units or glycerol monomers of the oligomeric polyglycerol. Typically, the polymerisation degree is given by the ratio between the molecular weight of the oligomer and the molecular weight of the monomer.

In certain embodiments of the disclosure the oligomers are obtained by condensing from 2 to 10 units of glycerol, wherein the lower is the glycerin dimer that is diglycerin.

In accordance with a further aspect, the disclosure relates to cosmetic compositions, in particular preparations for topical use, containing the polyglycerol-azelaic acid esters and/or polyesters described above. Preparations for topical use of the disclosure, rinse-off or otherwise, have properties which are suitable for applications in the field of cosmetics and dermatology.

In accordance with some preparation forms, polyglycerol-azelaic acid esters and/or polyesters are present in the cosmetic composition of this disclosure in a quantity of 0.01 to 20% by weight, preferably from 0.05 to 5% by weight. Typically, the cosmetic composition of this disclosure may be presented in any form suitable for local or topical application.

In some preparation forms, the disclosure composition comprises mixtures of polyglycerol-azelaic acid esters and/or polyesters as previously described and a cosmetically- and pharmaceutically-acceptable vehicle.

Typically, the disclosure composition can be presented in liquid form, such as a lotion, solution, suspension, shampoo or milk, or solid, semi-solid or fluid form, such as a cream or serum.

In some preparation forms the disclosure composition is in liquid form, for example in the form of an aqueous-based lotion containing one or more vehicles and/or excipients suitable for cosmetic applications.

In liquid form, the composition generally contains around 1 to 99.9% by weight of water. In some preparation forms, water is present in a quantity ranging between 5 and 95% by weight. In other preparation forms, water is present in a quantity between 10 and 90% by weight.

In some preparation forms, the vehicle for the disclosure composition is a base preparation for cosmetic formulations, typically for formulations of fluid preparations suitable for dermal or tricological applications.

In accordance with some preparation forms, the cosmetic composition containing polyglycerol-azelaic acid esters and/or polyesters may be a formulation for tricological use to be applied to hair, for example, a formulation which does not require rinsing (leave-on).

Leave-on formulations which are suitable for applying to the hair and/or scalp include, but are not limited to, aqueous lotions such as aqueous colloidal solutions or dispersions, hydroalcoholic lotions or hydroalcoholic colloidal solutions or dispersions, fluid emulsions, oil in water emulsions, hydrophilic gels, gelified aqueous or hydroalcoholic solutions which are formed by adding polymers, e.g. acrylic polymers such as Carbopol or high-molecular weight polyethylene glycols etc., to solvents, or serums.

According to other preparation forms, the cosmetic composition containing polyglycerol-azelaic acid esters and/or polyesters may be a formulation for tricological use to be applied to the hair, for example, a formulation which does require rinsing (rinse-off).

Rinse-off formulations which are suitable for applying to the hair and/or scalp include, but are not limited to, shampoos, cleansing systems containing surfactants, creams e.g. containing cationic substances (Polyquaternium, cetyltrimethylammonium chloride, Docosil trimethylammonium methyl sulphate, etc.), alcohols or high melting point fatty acids to be applied to wet (or dry) hair before or after shampooing and then rinsed, masks, e.g. containing cationic substances.

Applying the cosmetic composition of this disclosure to the skin or keratin structures results in the beneficial formation of a complex film, with protective film-forming characteristics.

By way of example, the compositions of this disclosure in liquid form can be prepared by dissolving the mixture of esters and polyesters or polyglycerol-azelaic acid polyesters of the type previously described in a fluid, typically water. Optionally, the resulting mixture may be buffered to reach a pH level compatible with that of skin, conveniently selected between pH 4 and 8.

In some preparation forms, the tricological composition of this disclosure may include excipients commonly used in the formulation of cosmetic preparations for local use, such as preservatives, bactericidal agents, stabilisers, emulsifiers, surfactants, buffers, humectants, dyes and other excipients commonly used in cosmetic/pharmaceutical preparation processes.

The disclosure composition may be applied, in an effective quantity, directly to the area to be treated, typically the skin of the face or body, scalp or hair. According to another aspect of the disclosure, a method of cosmetic treatment is provided which consists of local application, at the keratin structure level of the human body, of an effective amount of a cosmetic composition of the type previously described.

The mixtures and/or cosmetic compositions of this disclosure offer benefits in comparison with the cosmetic or dermatological use of azelaic acid, or cosmetic compositions in which it is an active principle.

Polyglycerol is safe for use and can form polymeric structures which are very different from each other, linear, branched and hyper-branched, with better solubility and cytotoxicity characteristics than polyethylene glycol polymers (used in known compositions). Furthermore, by selecting a specific molecular weight of the polyglycerol chain, it is possible to modulate the properties of the mixture and the formulations which contain it, these being chemical and physical properties, for example the solubility, or the absorption kinetics of the active ingredient, to achieve the preparation of modified forms of release of azelaic acid regulated by a chemical mechanism, due to the fact that the ester bond may, in certain conditions, be susceptible to in situ hydrolytic or enzymatic cleavage.

When applied to the skin, the polyesters of this disclosure, due to the presence of numerous hydroxyl groups which are able to form hydrogen bridges with as many water molecules, act as a polyfunctional reservoir of azelaic acid, which can form thin films on the skin, normalise it and hydrate it. The polyesters of this disclosure are therefore particularly beneficial in light of the greater tolerability compared with azelaic acid, in order to produce a sebum normalising action on the skin. In fact, it is known that at the level of the sebaceous glands the concentration of androgens is the most important regulating factor in sebum secretion. In particular, the 5-alpha reductase enzyme converts 4-androstenedione to dihydrotestosterone, a metabolite which can significantly increase sebaceous secretions.

A further benefit of the cosmetic use of polyglycerol-azelaic acid polyesters of this disclosure can be attributed to the antimicrobial action of azelaic acid, which produces an overall reduction in lipase activity of bacterial origin, associated with lower production of free fatty acids which determines the sebum normalising action on the skin.

Subsequent to these actions, the present disclosure provides for, according to a further aspect, the use of a mixture of esters and polyesters obtained by the process described above or polyglycerol-azelaic acid polyesters as previously described, for the treatment of skin irritation or inflammation conditions.

In accordance with some preparation forms, the disclosure relates to the use of a mixture of esters and polyesters obtained by the process described above or polyglycerol-azelaic acid polyesters as previously described, as a sebum-regulator for the skin.

In accordance with a further aspect of the present disclosure, it provides for the use of polyglycerol-azelaic acid polyesters of the type previously described to protect the skin, skin appendages or hair from heat or heat treatments.

Indeed, the Applicant has surprisingly found that the polyglycerol-azelaic acid esters and/or polyesters of this disclosure form a polymeric film when exposed to sources of heat or heat treatment.

This unexpected property of the polyglycerol-azelaic acid polyesters of this disclosure enables its application in the field of cosmetics for protecting the skin, its appendages or keratin fibres, and hair in particular, from heat treatments or exposure to heat sources such as sunlight.

In accordance with some preparation forms, polyglycerol-azelaic acid polyesters are added to cosmetic formulations for treating hair during washing or rinsing with water, for example shampoos and conditioners, in order to form a protective film over the hair's keratin structures during heat drying, such as with a hair dryer.

In some preparation forms, polyglycerol-azelaic acid polyesters are added to cosmetic formulations for treating hair which do not require washing after treatment in order to protect the hair from the effects of the sun's rays.

The present disclosure will now be described, making reference to the following examples which are provided solely for illustrative purposes and should not be understood as limiting the present disclosure.

The following source materials were used during the laboratory work referred to in the examples:
azelaic acid, CAS 123-99-9: A.C.E.F, Fiorenzuola d'Arda (Piacenza), Italy;
diglycerin, CAS 59113-36-9: Solvay Solexis;
polyglycerol-3, polyglycerol-4 and polyglycerol-6, CAS 25618-55-7: respectively Pure Vegetable PG-3, Pure Vegetable PG-4 and Pure Vegetable PG-6, Spiga Nord, Carasco (Genoa), Italy;
polyglycerol-10, CAS 25618-55-7: Natrulon H10, Lonza; Polyglycerol Pure Vegetable PG-3, preferred for the purposes of this disclosure, characterised with SEC testing before use, with the following values:

Mn=4818; Mw=4931; Mp=4693; D=1,023. The polydispersity index equal to 1.02 indicates a very pure product, essentially consisting only of polyglycerol-3 units.

EXAMPLE 1

This example refers to the production of polyglycerol-azelaic acid polyesters. Preparation of a batch (PGAO-02-01) of polyglycerol-azelaic acid polyesters:
The following were placed in a reactor:
560 g of polyglycerol-3
440 g of azelaic acid
0.25 grams of hypophosphorous acid
4 g of para-toluenesulfonic acid
The maximum temperature of the reaction was 175-180° C. The progress of the reaction was monitored by measuring the acidity index (on samples collected every 30 minutes using a sampler). The reaction time was approximately 2 hours. Operating under the process conditions described above, various polyglycerol-azelaic acid polyesters were produced, listed below as "Treatments", according to the following table:

TABLE 1

| Treatments | Glycerol oligomer used | Batch (Molar ratio azelaic acid-polyglycerol) | Reaction temperature (° C.) | Reaction time (mins) |
|---|---|---|---|---|
| 1 | Diglycerin | PGAO-01-01 (1:1) | 175 | 120 |
| 2 | Pure Vegetable PG-3 | PGAO-02-01 (1:1) | 175-180 | 120 |
|   |   | PGAO-02-02 (1:1.1) | 175-180 | 120 |
|   |   | PGAO-02-03 (1:1) | 180-185 | 40 |
|   |   | PGAO-02-04-(1:1) | 140-150 | 90 |
|   |   | PGAO-02-05 (1:1) | 150 | 6040 |
|   |   | PGAO-02-06/120 (2:1) | 150 | 360 |
|   |   | PGAO-02-07/150 (1:2) |   |   |
| 3 | Pure Vegetable PG-4 | PGAO-03-01 (1:1) | 175 | 120 |
| 4 | Pure Vegetable PG-6 | PGAO-04-01 (1:1) | 175 | 120 |
| 5 | Natrulon H10 | PGAO-05-01 (1:1) | 175 | 120 |

Of these polyesters, polyglycerol-azelaic acid polyesters PGAO-02-01 were characterised with SEC testing. See the chromatogram in FIG. 1. The test produced the following results: Mn=7722 Daltons; Mw=10,470 Daltons; D=1.356. The molecular weights (M.W.) are expressed as polystyrene equivalents Using the same SEC system and the same calibration for analysing the monomers (azelaic acid and polyglycerol-3) the following values are obtained:

Azelaic acid:
Mn=3064
Mw=3090
D=1.008
Polyglycerol-3:
Mn=4818
Mw=4931
D=1.023

Figure 1:
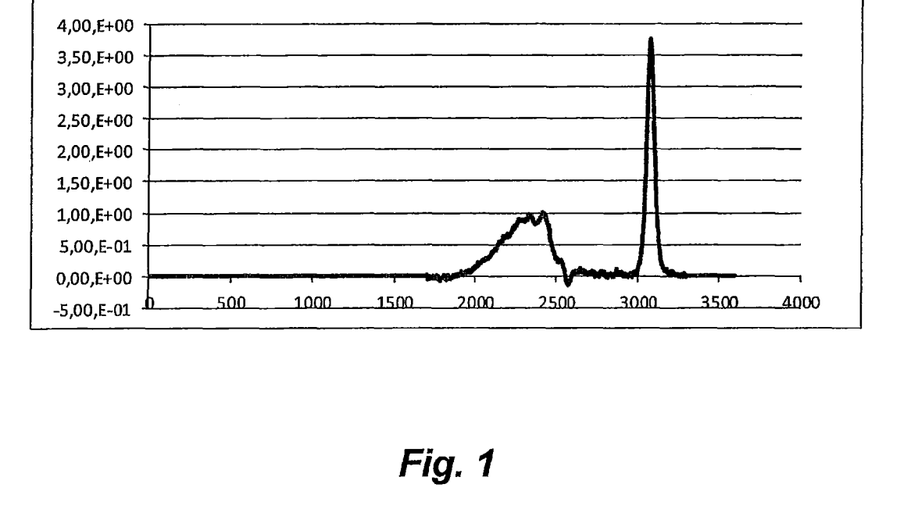
FIG. 1 shows the result of an SEC (Size Exclusion Chromatography) test on a polyglycerol-3-azelaic acid polyester according to the disclosure.

The average weight is very close to the sum of the weight of an azelaic acid molecule and a polyglycerol molecule, but the distribution of the weights indicates the presence of different species, which result from the condensation of more than one acid molecule and polyglycerol molecule, which evidently leads to the formation of oligomers.

Comparing the SEC chromatogram for this mixture with that of the source compounds shows that the product still contains the unreacted polyglycerol (overlap between the polyglycerol peak and one of the peaks of the product curve).

The SEC pattern shows that there is a significant presence of fractions of polymers with high molecular weights.

The SEC test was repeated on polyesters obtained with polyglycerol-3 using varying temperature conditions and molecular relationships between the reagents in order to reduce the presence of monoesters and increase fractions with higher molecular weights. These tests showed that the average molecular weight of the product increases as the reaction time increases.

EXAMPLE 2

This example relates to verifying the influence of the mixtures of this disclosure on the functional properties of formulations containing them.

In particular, the influence of mixtures in this disclosure on the formation and durability of foam in cleansing formulations was verified.

Formulations were prepared for testing constituting a simplified shampoo model, formed solely of water and the surfactant in question, added in a percentage equal to the active washing substance (12% according to the present example), as stated in "Estimated daily exposure levels for different cosmetic product types according to Colipa data", SCCNFP/0321/02; Hall et al. 2007, 2011). An anionic surfactant was chosen, as these surfactants are known to be the most susceptible to hard and very hard water.

The tests were carried out on a formulation containing a mixture of this disclosure produced in Example 1 and, for comparison, on a "blank".

The formulation according to the disclosure was prepared by weighing 4.650 g of Sulfetal LA (anionic active matter 27%, for a total of 1,255 g of ammonium lauryl sulphate), 0.120 g of Treatment 2—PGAO-02-01, and demineralised water sufficient for 10,460 g, homogenising all the components with a magnetic stirrer for 5 minutes.

The comparison formulation was prepared by weighing 4.650 g of Sulfetal LA and demineralised water sufficient for 10,460 g and homogenising these components with a magnetic stirrer for 5 minutes.

250 g of water of a controlled composition and classified as hard was added to both these samples. The analytical data of this water is: bicarbonate 574 mg/l; nitrate 6.9 mg/l; sodium 74.4 mg/l; calcium 171 mg/l; magnesium 27.8 mg/l; fixed residue at 180° C.=752 mg/l; electrical conductivity at 20° C.=1123 µS; pH 5.8; both sample 1, the disclosure, and sample 2, the "blank" sample, were prepared in this way.

The two samples underwent testing for the formation and durability of foam, performed using the SITA Foam Tester instrument (SITA Messtechnick GmbH, Dresden). This instrument is described in detail in patent EP 1092970 and enables automatic sampling, heating and temperature control of the sample by means of a double jacket in the vessel which houses the test sample. A sensor allows precise adjustment of the sample temperature. For this purpose, the instrument was used alongside a MLW 4 thermostat (VEB MLW Prüfgeräte—Werk, Medingen, Germany).

Foam formation is achieved with a rotor which enables the amount of air within the sample to be regulated. The measurement of the volume of foam and its deterioration over time are carried out using needle-shaped sensors which can measure the profile in many points in the sample's surface.

For testing, the samples are loaded into the instrument's reservoir which carries out automatic sampling of 250 ml of the product and starts the test, according to an agitation cycle at 1250 rpm for 120 seconds. The sample temperature is maintained at 44° C.+/−1° C. (representative of a hot shower). The foam is measured every 60 seconds over a period of 15 minutes.

The results of the test are reported in Table 2

TABLE 2

| Time (mins) | Foam volume (ml) | |
| --- | --- | --- |
| | Sample 1 (disclosure) | Sample 2 (blank) |
| 1 | 950 | 950 |
| 2 | 947 | 946 |
| 3 | 940 | 941 |
| 4 | 935 | 936 |
| 5 | 931 | 930 |
| 6 | 929 | 925 |
| 7 | 928 | 924 |
| 8 | 925 | 917 |
| 9 | 925 | 913 |
| 10 | 921 | 911 |
| 11 | 920 | 908 |
| 12 | 915 | 903 |
| 13 | 911 | 901 |
| 14 | 908 | 898 |
| 15 | 904 | 893 |
| 16 | 899 | 888 |

As can be seen from the data in Table 2, the presence of the mixture of this disclosure does not substantially alter the durability properties of the foam from the water-based surfactant composition.

The same test was carried out with other anionic and amphoteric surfactants, such as disodium laureth sulfosuccinate, disosium laureth sulphate, disodium amphodiacetate, on formulations containing mixtures of this disclosure in a range between 0.1 and 3% by weight, without detecting significant differences related to the formation and stability of the foam.

EXAMPLE 3

Formulations for cosmetic use containing polyglycerol-azelaic acid polyesters, obtained by condensing the linear glycerol trimer and azelaic acid according to example 1.

Formulation 1 - RESTRUCTURING LOTION

| Component (chemical name/INCI) | Concentration w/w (%) |
| --- | --- |
| Denatured alcohol type C | 13.00-18.00 |
| PEG - 40 Hydrogenated castor oil | 0.10-0.50 |
| VP/VA Copolymer | 0.01-0.05 |
| Parfum | 0.05-0.20 |
| Polyglycerol-azelaic acid polyesters | 0.05-1.80 |
| Water | sufficient for 100 |

Formulation 2 - SEBUM-NORMALISING SHAMPOO

| Component (chemical name/INCI) | Concentration w/w (%) |
| --- | --- |
| Disodium Laureth Sulfosuccinate | 1.00-7.00 |
| Di-PPG-2-Mireth-10 Adipate | 0.50-3.00 |
| Disodium Cocoamphodiacetate | 0.50-3.00 |
| Ammonium Lauryl Sulfate | 0.50-3.00 |
| Polyquaternium-10 | 0.10-0.50 |
| Tetrasodium EDTA | 0.05-0.20 |
| Parfum | 0.10-1.50 |
| Hydroxypropyltrimonium Hydrolysed Corn Starch | 0.05-1.00 |
| BHA | 0.005-0.015 |
| Potassium chloride | 0.50-1.50 |
| Dimethicone PEG-7 Isostearate | 0.5-1.50 |
| PEG-120 Methyl Glucose Dioleate | 0.10-0.90 |
| Laureth-3 | 0.01-0.80 |
| PEG-90 Glyceryl Isostearate | 0.10-0.80 |
| PEG-8 Caprylyc/Capric Glycerydes | 0.50-1.00 |
| Polyglycerol-azelaic acid polyesters | 0.05-1.80 |
| Sodium Hydroxymethylglycinate | 0.20-0.45 |
| Citric acid | sufficient for pH 5.5-6.0 |
| Water | sufficient for 100 |

Formulation 3 - TRICOLOGICAL SERUM

| Component (chemical name/INCI) | Concentration w/w (%) |
| --- | --- |
| Denatured alcohol type C | 15-20 |
| Hydrogenated castor oil | 0.50-0.9 |
| Parfum | 0.01-0.05 |
| Hydroxypropyl guar | 0.1-0.8 |
| Polyglycerol-azelaic acid polyesters | 0.05-1.80 |
| Water | sufficient for 100 |

Formulation 4 - CONDITIONING CREAM

| Component (chemical name/INCI) | Concentration w/w (%) |
| --- | --- |
| Behentrimonium Methosulfate | 0.5-3.0 |
| Panthenol | 0.5-3.0 |
| Cetearyl Alcohol | 0.5-4.0 |
| Palmitic acid | 0.5-4.0 |
| Mirystic acid | 0.5-4.0 |
| Hydrolysed Wheat Protein | 0.05-1.0 |
| Cetrimonium Chloride | 1.0-3.0 |
| Penthylene glycol | 5.0 |
| Phenoxyethanol | 0.5-1.0 |
| Parfum | 0.1-0.3 |
| Polyglycerol-azelaic acid polyesters | 0.05-1.80 |
| Water | sufficient for 100 |

Formulation 5 - BODY MILK

| Component (chemical name/INCI) | Concentration w/w (%) |
| --- | --- |
| Glycerin | 1.00-6.00 |
| Methylpropanediol | 1.00-6.00 |
| Cetyl hydroxyethylcellulose | 0.10-0.40 |
| Xanthan gum | 0.10-0.40 |
| Tapioca starch | 1.00-2.00 |
| Disodium EDTA | 0.025-0.20 |
| Sorbitan stearate | 2.00-5.00 |
| Sucrose cocoate | 0.10-1.00 |
| Ethylexyl palmitate | 1.00-5.00 |
| Hydrogenated polydecene | 1.00-5.00 |
| Caprilic/capric triglycerides | 1.00-5.00 |
| *Butyrospermum parkii* | 1.00-5.00 |
| Meadowfoam (*Limnanthes alba*) seed oil | 1.00-3.00 |
| Dimethicone | 1.00-5.00 |
| Sodium hydroximethylglycinate | 0.10-0.20 |
| Polyglycerol-azelaic acid polyesters | 0.05-1.80 |
| Phenoxyethanol | 0.70-0.90 |
| Lactic acid | sufficient for pH 5.5-6.0 |

Formulation 5 - BODY MILK

| Component (chemical name/INCI) | Concentration w/w (%) |
|---|---|
| Parfum | 0.30 |
| Delta tocopherol | 0.02-0.25 |
| Sorbityl furfural | 0.10-0.90 |
| Water | sufficient for 100 |

Formulation 6 - LEAVE-ON CLEANSER

| Component (chemical name/INCI) | Concentration w/w (%) |
|---|---|
| Glycerin | 2.00-5.00 |
| Ethylhexylglycerin | 0.25-0.50 |
| Octatrienoic acid | 0.05-0.50 |
| Trehalose | 0.50-1.00 |
| Potassium hydroxide | sufficient for pH 5.5-6.0 |
| PPG-26 Buteth-26 | 2.00-15.00 |
| PEG-40 Hydrogenated Castor Oil | 2.00-15.00 |
| Methylpropanediol | 1.00-6.00 |
| Polyglycerol-azelaic acid polyesters | 0.05-1.80 |
| Water | sufficient for 100 |

EXAMPLE 4

The anti-inflammatory effects were investigated of polyglyceryl-3 azelaiate oligomers (POLY-AZ) obtained with the method in Example 1 in an in vitro model of inflammation on human keratinocytes NCTC2544, and using lipopolysaccharide
(LPS) from *E. coli* to mediate inflammation or irritation. The effect of the derivative in the models used was compared with that of azelaic acid (AZ-ACID), a known anti-inflammatory agent.

The irritant potential of the derivative (POLY-AZ) was also determined in vitro compared with a positive control (cells treated with 5 μg/ml of lipopolysaccharide). The results were compared with those obtained using azelaic acid (AZ-ACID) in the same experimental model.

Materials
Biological Model

The human keratinocyte cell line NCTC 2544 (Perry V. P. et Al., 1957) was obtained from the Istituto Nazionale per la Ricerca sul Cancro [National Institute for Cancer Research], Genoa, Italy.

Cultivation and Propagation of the Cell Line

Using the immortalised human keratinocyte cell line NCTC 2544 (Perry V. P. et al., 1957) cultured in sterile flasks (25 cm$^3$), incubated at 37° C. in a wet atmosphere at 5% CO$_2$ in MEM (Minimum Essential Medium) culture medium supplemented with 10% fetal bovine serum (FBS), 2 mM glutamine, 1% non-essential amino acids, in the presence of 1% penicillin and streptomycin.

1:3 splitting is carried out every 2 days when monolayer is formed by washing with PBS 1× (phosphate buffer without Ca$^{2+e}$ Mg$^{2+}$) and cell separation with a trypsin-EDTA solution at 37° C. for 2 minutes.

Reagents and Equipment Used

| REAGENTS | COMPANY |
|---|---|
| EMEM (EBSS) without L-glutamine | Lonza (BE12-125F) |
| Amino Acids Solution (100X) | Lonza (BE13-114E) |
| FBS ES | Lonza (DE14-850F) |
| PEN STREP MIX (Penicillin 10,000 UI/ml, Streptomycin 10,000 UI/ml) | Lonza (DE17-602F) |
| L-glutamine 200 mM | Lonza (BE17-605E) |
| DMSO | SIGMA (D1435) |
| PBS 1X without Ca+ and Mg2+ | Lonza (BE17-516F) |
| Trypsin-Versene (EDTA) Mixture (1X) | Lonza (BE17-161E) |
| Trypan Blue | Sigma (T8154-20ML) |
| MEM Eagle EBSS (2X), w/o L-Gln, phenol red | Lonza (BE12-668-E) |
| MTT | Sigma (M2128 1G) |
| Chloroform | Sigma (366919) |
| Agarose | Sigma (A9539) |
| Ethidium bromide solution | Sigma (E1510) |
| Gel Loading Buffer | Sigma (G2526) |
| Tri-Reagent | Sigma (T9424) |
| 2-Propanol | Sigma (59304) |
| Tris Acetate-EDTA buffer | Sigma (T9650) |
| Water | Sigma (95284) |
| High Capacity cDNA Reverse Transcription Kit | Applied Biosystems (4368814) |
| TaqMan ® Universal PCR Master Mix, No AmpErase ® UNG | Applied Biosystems (4324018) |
| Lipopolysaccharides from *E. coli* | Sigma (L4391) |

| EQUIPMENT | COMPANY |
|---|---|
| Inverted phase contrast microscope | Leica |
| Laminar flow hood | Sterile Manufacturing Division |
| HeraCell CO2 incubator (Mod: 150 ADV) | Thermo Scientific |
| Digital water bath | Stuart |
| Chest freezer −80° C. | Elcold |
| Burker chamber | Carlo Erba |
| Scale (Mod. AM100) | Mettler |
| Microplate spectrophotometer (Mod: ELX808) + Gen5 Software | BioTek |
| UV-visible spectrophotometer (MOD: 6715, BS-6715B0) | JenWay |
| Analogue vortex mixer (Mod. Sa8, BS-SAB) | Stuart |
| Real time PCR system (Mod: Mx3000P) | Stratagene |
| Dell PC + MX3000P Software versions 1.2 and 2.00 | Stratagene |
| Trans-UV (ACDM-ECXF15M) | Vilber Lourmat |
| Horizontal electrophoresis chamber (MOD: 250-5159) | Ward |
| Power supply for electrophoresis chamber (MOD: 250-5159) | Ward |
| Digital camera + UV protection device (S630) | Samsung |
| Bench-top centrifuge (Galaxy 7d) | VWR |
| Mixer (TR13) | Girmy |

Active Compounds Tested

| | NAME | |
|---|---|---|
| | POLY-AZ | AZ-ACID |
| NAME/UNIQUE IDENTIFIER | Polyglyceryl-3-azelaiate oligomers (Example 1) | Azelaic acid (A.C.E.F.) |
| STORAGE | rt | rt |
| CONCENTRATION | 20 μM* | 20 μM* |

*All concentrations are related to the active compound in the usage matrix

Control

Negative control: Human keratinocytes NCTC2544 cultured in EMEM (EBSS) at 2.5% FBS, supplemented with 2 mM L-glutamine, 1% amino acid solution and 1% penicillin (10,000 U/ml)/streptomycin (10,000 Ug/ml) mixture at 37° C., 5% $CO_2$.

Positive control: Human keratinocytes NCTC2544 treated with LPS (5 µg/ml) in EMEM (EBSS) at 2.5% FBS, supplemented with 2 mM L-glutamine, 1% amino acid solution and 1% penicillin (10,000 U/ml)/streptomycin (10,000 Ug/ml) mixture a 37° C., 5% $CO_2$.

Methods

The TNF-α gene expression in NCTC 2544 was evaluated using RT-PCR.

There are four phases to the gene expression analysis:
1. Treatment of cells with active compounds for 16, 24 and 48 hours;
2. RNA extraction;
3. cDNA reverse transcription;
4. Real-time quantitative PCR.

Handling of NCTC2544 Cells

Under experimental conditions, in connection with the results obtained in a previous MTT assay (data not shown), polyglyceryl-3-azelaiate and azelaic acid were tested at a concentration of 20 µM (final concentration in the medium). Both positive and negative controls were tested.

Anti-Inflammatory Test on NCTC2544

Day 1: Cell Seeding

When the cells (human keratinocytes NCTC 2544) reached approximately 80% confluence, they were separated with trypsin/EDTA and seeded at a density of $1 \times 10^6$ cells/ml in a 12-well plate and then incubated at 37° C., 5% CO2 (24 hours).

Day 2: 24-Hour Exposure to Substances

Polyglyceryl-3-azelaiate and azelaic acid were dissolved in DMSO (100%) at a concentration of 25 mM (stock solution), and then diluted in EMEM, supplemented with 2.5% FCS, 2 mM L-glutamine, 1% NEAA solution and 1% penicillin (10,000 U/ml)/streptomycin (10,000 pg/ml).

The controls, containing only culture medium (negative control) and the culture medium plus LPS (5 µg/ml) (positive control) were included in each plate.

The cells were exposed to 20 µM of the compounds. LPS in a concentration of 5 µg/ml was added to each well (with the exception of the negative control). The test was replicated for each compound.

Test of Irritancy Potential in NCTC2544

Day 1: Seeding

When the cells (human keratinocytes NCTC 2544) reached approximately 80% confluence, they were separated with trypsin/EDTA and seeded at a density of $1 \times 10^6$ cells/ml in a 12-well plate and then incubated at 37° C., 5% CO2 (24 hours).

Day 2: 24-Hour Exposure to Substances

Polyglyceryl-3-azelaiate and azelaic acid were dissolved in DMSO (100%) at a concentration of 25 mM (stock solution), and then diluted in EMEM, supplemented with 2.5% FCS, 2 mM L-glutamine, 1% NEAA solution and 1% penicillin (10,000 U/ml)/streptomycin (10,000 pg/ml).

The controls, containing culture medium (negative control) and the culture medium plus LPS (5 µg/ml) (positive control) were included in each plate.

The cells were exposed to 20 µM of the active compounds. The cells were then incubated at 37° C., 5% CO2 for 24 hours.

RNA Extraction

Total RNA was extracted from the cells using Tri Reagent (Sigma Aldrich), which is a single homogeneous solution for RNA isolation according to the supplier's indications.

The purity of the extracted total RNA was evaluated by measuring the absorbance at 260 nm, the A in which the nucleic acid has the maximum absorbance. The absorbance at 280 nm was also measured, to evaluate contamination with proteins or phenol. RNA is considered good quality if the A260/A280 ratio=R is >1.4.

After determining the total RNA concentration and the purity of each RNA sample, it was diluted in DEPC-treated water to a final concentration of 2 µg/ml. This is the concentration required by the reverse transcription kit. Gel electrophoresis was also performed to verify the integrity of the extracted total RNA.

Reverse Transcription PCR

The extracted and quantified total RNA was amplified using the "High Capacity cDNA Reverse Transcription Kit" (Applied Biosystems).

Random primers were used to ensure efficient first-strand mRNA synthesis.

The RT-PCR System Mx3000P (Stratagene) was used for the amplification, and each total RNA was amplified in duplicate.

| Amplification conditions | Step 1: | Step 2: | Step 3: | Step 4: |
|---|---|---|---|---|
| Temperature | 25° C. | 37° C. | 85° C. | 25° C. |
| Time | 10 mins | 120 mins | 60 secs | hold |

After amplification, samples were diluted with 30 pl of DEPC-treated water and stored at −20° C. until use.

Real Time PCR

The RT-PCR was set up using linear TaqMan probes (Applied Biosystems). These probes are the most common and publicised detection system for qPCR applications.

The inventoried probes and primers were chosen on the strength of previous specific bibliographical studies.

The relative quantification method was used which compares the relative concentration of the gene of interest (target) in unknown samples to a calibrator or control sample (untreated cells). Here, the calibrator is a baseline for the expression of a target gene.

The following genes were used:

| GENE NAME | TAQMAN ASSAY ID | Amplification schedule | Amplicon length |
|---|---|---|---|
| GAPDH (housekeeping) | Hs99999905_m1 | 95° C. 15 s<br>60° C. 60 s<br>For 40 cycles | 122 |
| TNF-α (target) | Hs00174128_m1 | 95° C. 15 s<br>60° C. 60 s<br>for 40 cycles | 105 |

Test Procedure

The RT-PCR was performed using the cDNA of cells treated with different treatment times and control cells.

10 µl of Mix 2× Gene Expression master TaqMan and 1 µl of 20× Gene Expression TaqMan were added to the cDNA. Each biological sample was treated in duplicate and amplified as indicated in the table.

| | STEP | | |
|---|---|---|---|
| | Step 1: UDG incubation | Step 2: Activation of AmpliTaq Gold DNA Polymerase | Step 3: PCR Cycle (50 cycles) |
| | Hold | Hold | Denature | Anneal/Extend |
| Temperature | 50° C. | 95° C. | 95° C. | 60° C. |
| Time | 2 mins | 10 mins | 15 secs | Hold |

Data Collection

The data provided by the Stratagene Mx3000P tool was recorded by the MXpro v.4.01 software. When the amplification was complete, the software automatically applied the $2^{-\Delta\Delta}$ Ct method. The Ct values of the target and the normaliser should ideally be within approximately ten cycles of one another.

Comparative quantisation produces a relative comparative diagram. A value equal to one indicates no change in the gene expression of the target gene between the study sample and the calibrator, while a value greater than one indicates up-regulation and less than one indicates down-regulation. A value is considered significant if it is at any time greater or less (up-regulated or down-regulated) in comparison with the calibrator.

Results

TNF-α is usually over-expressed in the epidermis of patients with psoriasis (Kristensen et al, 1993; Ettehadi et al, 1994) and has a pivotal role in the pathogenesis of the disease itself. The main role of TNF-α is also supported by evidence that, in psoriasis, other TNF-α-regulated genes are over-expressed and that TNF-α antagonists are used as highly-effective therapeutic agents in most patients (Richardson and Gelfand, 2008). It has recently been suggested that TNF-α inhibits barrier protein expression (for example, FLG and LOR), that TNF-α antagonists may contribute to the clinical improvement of psoriasis patients by increasing barrier protein expression (Kim et al., 2011).

McRitchie et al. (1997) recently demonstrated that 10 μg/ml of LPS from *E. coli* maximally stimulated TNF-α production by alveolar epithelial cells within 4 hours.

In the study undertaken, it was found that treatment with LPS from *E. coli* (5 μg/ml) had a stimulatory effect on TNF-α production and therefore the inflammatory process of NCTC 2544 cells from 16 hours of treatment.

An experiment to verify the effects of LPS on the NCTC 2544 cell line was initially set up. Treatments were carried out with LPS (5 μg/ml) in EMEM with a low FBS (2.5%) content for 16, 24 and 48 hours and TNF-α stimulation was evaluated.

From 16 hours, incubation with LPS produces significant TNF-α production (gene expression) compared to the negative control.

After 24 hours of treatment with LPS (5 μg/ml) the TNF-α gene expression was significantly (P<0.05) increased by around three times, and this effect is maintained even after 48 hours of incubation, although to a lesser extent.

On the basis of the results obtained, subsequent assays were carried out after 24 hours of incubation corresponding to a greater TNF-α stimulation by LPS.

Inflammation Assay

Following the preliminary model validation experiment described above, the TNF-α gene expression was evaluated using RT-PCR on NCTC 2544 cells, after treatments with 20 μM of polyglyceryl-3-azelaiate and 20 μM of azelaic acid together with LPS at 5 μg/ml in the culture medium to evaluate the anti-inflammatory effect of the two compounds.

After 24 hours of treatment (FIG. 2), azelaic acid does not produce an inhibitory effect on TNF-α gene expression, while polyglyceryl-3-azelaiate has a significant inhibitory effect (P<0.05).

Irritation Assay

The TNF-α gene expression in NCTC 2544 cells was also evaluated after treatments with 20 μM of polyglyceryl-3-azelaiate and 20 μM of azelaic acid compared with cells treated with LPS (5 μg/ml) in the culture medium, in order to compare the effects of these compounds against a known irritant agent (LPS).

During the inflammation test, after 24 hours of incubation (FIG. 2), treatment with polyglyceryl-3-azelaiate acid produced a significant (P<0.05) down-regulation of TNF-α compared with the positive control. In particular, in this test evaluating the irritancy potential of the two substances, neither are irritating, but polyglyceryl-3-azelaiate is more effective than azelaic acid (reduction by about half) in its down-regulation.

The experiments conducted show that at 20 μM, polyglyceryl-3-azelaiate was well-tolerated by the system used.

In terms of the anti-inflammatory effect, (a marked increase in TNF-α gene expression was observed after treatment with LPS 5 μg/ml compared with untreated cells) polyglyceryl-3-azelaiate demonstrated an anti-inflammatory effect (reduction of TNF-α) and this effect is greater than with azelaic acid. Also when tested in vitro for their irritancy potential on human keratinocytes NCTC 2544, after 24 hours of incubation, polyglyceryl-3-azelaiate was more effective in down-regulating TNF-α gene expression compared with the same concentration of azelaic acid.

Figure 2:
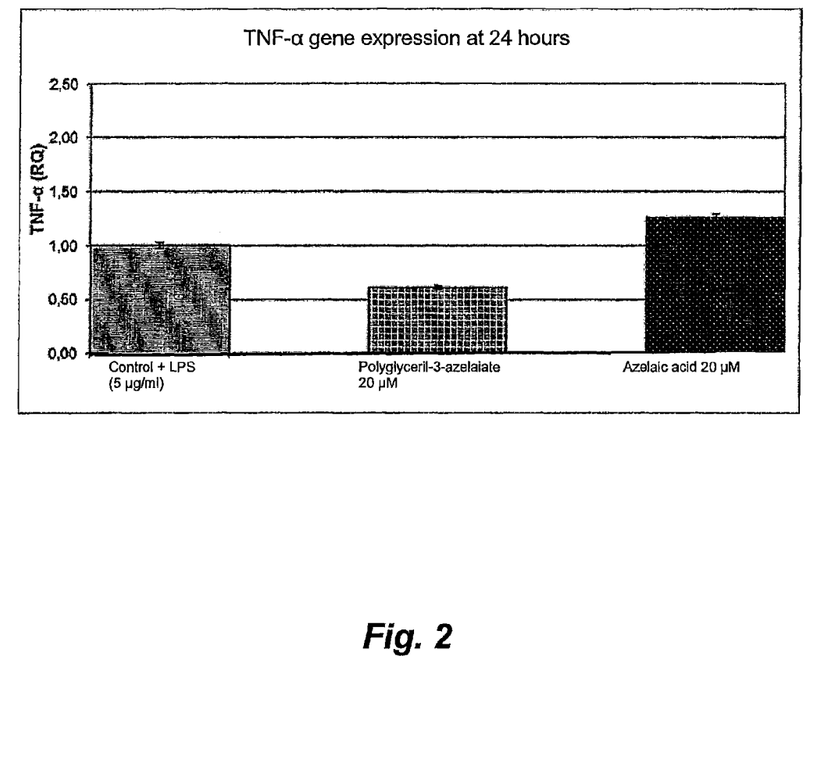
FIG. 2 shows a block chart illustrating the anti-inflammatory activity of the polyglycerol-3-azelaic acid polyester as per the disclosure compared to azelaic acid.
Figure 3:
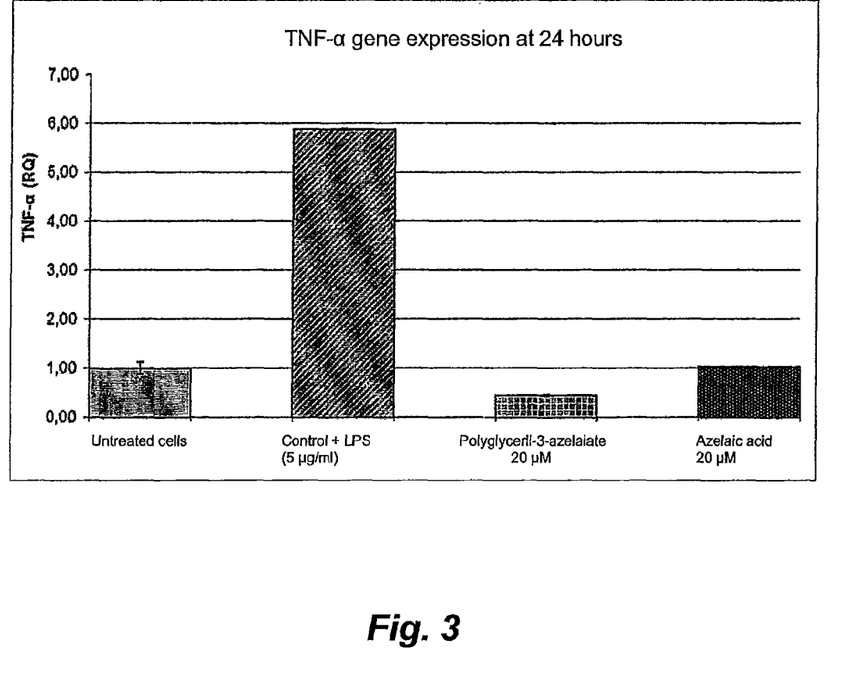
FIG. 3 shows a block chart illustrating the irritant action of the polyglycerol-3-azelaic acid polyester as per the disclosure compared to azelaic acid.

Description of FIGS. 2 and 3 relating to the experimental portion:

FIG. 2 illustrates the tumour necrosis factor-alpha (TNF-α) gene expression in human keratinocytes NCTC 2544 as determined by RT-PCR. NCTC 2544 cells were treated for 16, 24 and 48 hours, at 37° C. in CO2 at 5%, con: LPS (5 μg/ml), LPS (5 μg/ml)+polyglyceryl-3-azelaiate 20 μM and with LPS (5 μg/ml)+azelaic acid 20 μM. The values are the average of 2 experiments carried out in duplicate.

FIG. 3 illustrates the tumour necrosis factor-alpha (TNF-α) gene expression in human keratinocytes NCTC 2544 as determined by RT-PCR. NCTC 2544 cells were treated with: base culture medium, containing 2.5% fetal bovine serum (negative control) and with: base culture medium, containing 2.5% fetal bovine serum to which was added LPS (5 μg/ml) (positive control); with base culture medium, containing 2.5% fetal bovine serum and polyglyceryl-3-azelaiate 20 μM; with base culture medium, containing 2.5% fetal bovine serum and azelaic acid 20 μM. The values are the average of 2 experiments carried out in duplicate.

EXAMPLE 5

Foreword

During the tests carried out to identify the most suitable synthesis conditions for obtaining polyglycerol-azelaic acid polyesters, it was observed that the application of increasing temperatures promotes crosslinking of the polymer/polyester.

In some cases, the polyglycerol-azelaic acid polyester based product, as it existed at the end of the process, appeared as an elastic solid with an opaque, gel-type appearance.

Consequently topical applications of polyglycerol-azelaic acid polyesters were tested in cases where the skin or skin appendages are exposed to heat, for example during exposure to solar radiation during warmer periods of the year or to direct or indirect heating systems (hot plates, hair dryers, hairdressers' helmet dryers, etc.).

It is known that such treatments can cause stress to the hair, especially when they are used frequently.

An ad hoc test was therefore set up to verify this observation.

Introduction

Temporary straightening of hair by applying heat with a heated plate is an increasingly common technique in the field of hair styling.

Tests were conducted on the effects of prolonged heat treatment, using commercial hair straighteners (GA.MA Italy, Professional Line, mod. Art. 100), on the hair fibre's cuticular structure.

The process of straightening hair using commercial hair straighteners subjects the hair to thermal stress, in particular if the heat treatment is performed in a continuous manner and in close proximity.

Scope of the Laboratory Work

The objective of the test procedure below was to develop a method to verify the protective efficacy of two different formulations (shampoo and leave-on product) containing polyglyceryl-3-azelaiate after application to donated locks of hair which had never previously been treated when faced with prolonged thermal stress from using a commercial hair straightener (GA.MA Italy, Professional Line, Mod ART. 100). A formulation (shampoo) with no active ingredient was used as a negative control during the tests. Locks of hair from the same donor, which had not been subjected to any thermal stress, were used as a positive control.

Materials

Formulations Tested

The formulations below were prepared:

| Formulation - shampoo ACTIVE | |
|---|---|
| INCI | % w/w |
| WATER | SUFFICIENT FOR 100 g |
| WATER, AMMONIUM LAURYL SULFATE (AQUEOUS SOLUTION AT 27% OF SURFACTANT) | 6500 |
| WATER, DISODIUM LAURETH-3 SULFOSUCCINATE (AQUEOUS SOLUTION AT 38% OF SURFACTANT) | 14,500 |
| POTASSIUM CHLORIDE | 1000 |
| WATER, DISODIUM COCOAMPHODIACETATE (AQUEOUS SOLUTION AT 28% OF SURFACTANT) | 7000 |
| POLYGLYCERYL 3 AZELAIATE OLIGOMERS | 1000 |
| CITRIC ACID | SUFFICIENT FOR pH 5.5 |

| Formulation - leave-on ACTIVE | |
|---|---|
| INCI | % w/w |
| WATER | SUFFICIENT FOR 100 g |
| POLYGLYCERYL 3 AZELAIATE OLIGOMERS | 2000 |
| SODIUM HYDROXIDE | SUFFICIENT FOR pH 4.5 |

Positive Control

Locks of hair from the same donor, which had not been subjected to any heat treatment (the locks of hair were taken before heat treatment was commenced).

Negative Control

In order to determine the protective potential of the active ingredient tested, a shampoo formulation without polyglyceryl-3-azelaiate was simultaneously prepared, according to the following formulation:

| Formulation - shampoo PLACEBO | |
|---|---|
| INCI | % w/w |
| WATER | SUFFICIENT FOR 100 g |
| WATER, AMMONIUM LAURYL SULFATE (AQUEOUS SOLUTION AT 27% OF SURFACTANT) | 6500 |
| WATER, DISODIUM LAURETH-3 SULFOSUCCINATE (AQUEOUS SOLUTION AT 38% OF SURFACTANT) | 14,500 |
| POTASSIUM CHLORIDE | 1,000 |
| WATER, DISODIUM COCOAMPHODIACETATE (AQUEOUS SOLUTION AT 28% OF SURFACTANT) | 7000 |
| CITRIC ACID | SUFFICIENT FOR pH 5.5 |

Study Model 3 locks of hair from the same donor, never previously treated, chestnut in colour and 25 cm long, arranged in equal weight locks (approximately 10 g).

Test Procedure

1. Preparation of 3 locks of untreated donated hair, of approximately 10 g each;
2. Collection of 2 hairs (positive control) for subsequent microscopic analysis;
3. Fixing of a lock of hair to a suitable frame which keeps it steady during the subsequent phases;
4. The lock underwent repeated brushing (alternating 10 brushes on the front and 10 on the back), for 4 minutes;
5. The first cycle of thermal stress was started:

Application of commercial hair straighteners (GA.MA Italy, Professional Line, Mod. ART. 100) continuously for 15 seconds, along the entire length of the lock;

This 15-second thermal stress was repeated a further 5 times;

6. The lock was rinsed under running water (approx. 44° C. constant flow) for one minute;
7. 1 mL of the PLACEBO or ACTIVE shampoo formulation was applied evenly to the entire lock for 1 minute (dispersed over the lock then gently massaged with the fingertips);
8. The formulation was left for a further minute and then rinsed under running water (approx. 44° C. constant flow) for one minute;
9. The lock was gently wrung out and dried with absorbent paper towel and then reattached to the frame.

LEAVE-ON APPLICATION: in this case only, after shampooing with the PLACEBO formulation, 1 mL of Leave-on formulation was applied evenly to the lock;

10. The lock of hair was dried, without brushing or combing, using a hair dryer (Turbo Action Professional, Mod. ST. 30005) from which the air was applied on the highest heat setting, at medium power, from a distance of approximately 4 cm from the lock and for a duration of 4 minutes.
11. At the end of the first heat cycle, the hairs and hair fragments collected on the sheet at the base of the frame were carefully collected, counted and stored for subsequent microscopic analysis;
12. The lock of hair underwent the same heat cycle a further two times according to the specifications listed above;

13. At the end of the third heat cycle the lock was combed (front and back) with a fine-toothed comb for approximately 1 minute;

14. Fragments of hair approximately 2-3 cm in length from each heat cycle underwent subsequent microscopic analysis to assess the damage from thermal stress.

Data Processing

For each of the three formulations tested microscope observation was performed on the fragments of hair collected at the base of the frame and resulting respectively from the first and third heat treatments. The images were studied with a phase contrast microscope (Leica DM 2000) at 100× oil immersion magnification. For each fragment digital images of 5 different points of the fragment were acquired. Each observation was carried out in duplicate at least.

Figure 4:
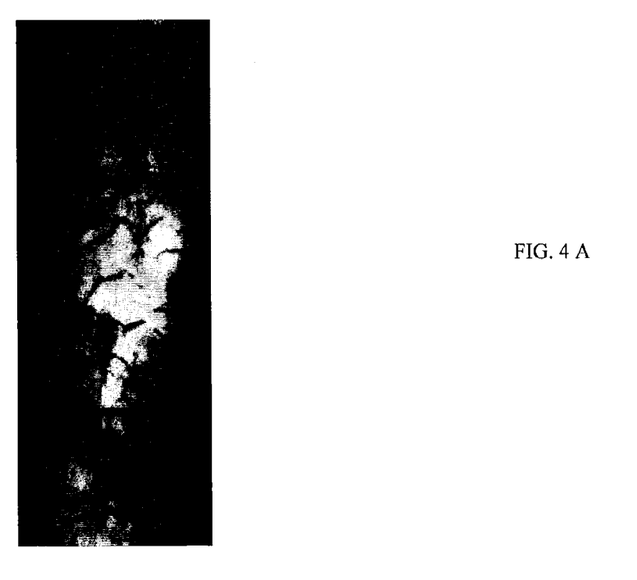
FIG. 4A shows a microscopic image of a fragment of untreated hair.
FIG. 4B shows a microscopic image of a fragment of hair which has undergone heat treatment after preliminary treatment with a placebo formulation.

FIG. 4A shows the microscope image of an untreated fragment of hair (unstressed), unstressed and originating from a donor lock 25 cm long and brown in colour/3. The hair shown was not treated.

FIG. 4B shows the microscope image of a treated fragment of hair (stressed), originating from a never-treated donor lock, 25 cm long and brown in colour/3. The lock of hair underwent three consecutive cycles of thermal stress, as stated in the test procedure. At the end of each heat cycle, the hairs were collected and studied under a microscope at 100× oil immersion magnification The hair shown was treated with the placebo formulation.

Figure 5A:
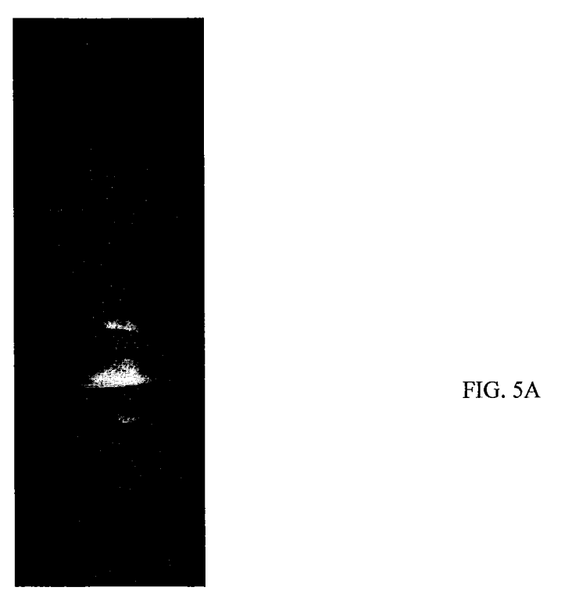
FIG. 5A shows a microscopic image of a fragment of hair which has undergone heat treatment after preliminary treatment with a rinse-off formulation containing polyglycerol-azelaic acid polyesters.

FIG. 5A shows the microscope image of a treated fragment of hair (stressed), originating from a never-treated donor lock, 25 cm long and brown in colour/3. The lock of hair underwent three consecutive cycles of thermal stress, as stated in the test procedure. At the end of each heat cycle, the hairs were collected and studied under a microscope at 100× oil immersion magnification The hair was treated with a rinse-off formulation (shampoo), formulated using polyglycerol-azelaic acid polyesters.

Figure 5B:
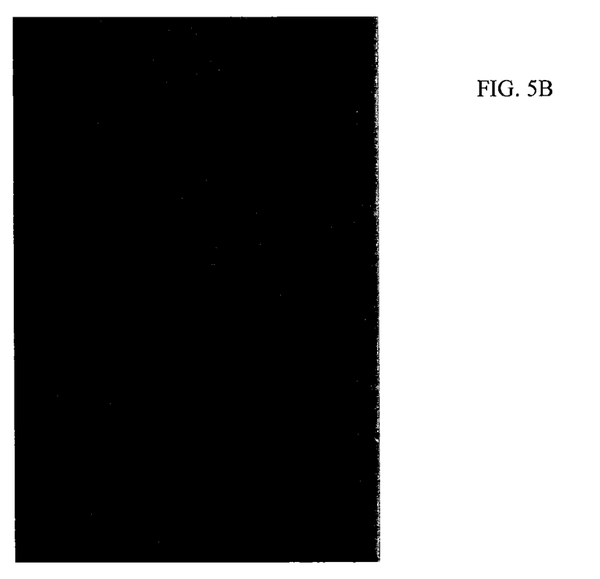
FIG. 5B shows a microscopic image of a fragment of hair which has undergone heat treatment after preliminary treatment with a leave-on formulation containing polyglycerol-azelaic acid polyesters.

FIG. 5B shows the microscope image of a treated fragment of hair (stressed), originating from a never-treated donor lock, 25 cm long, weighing 10 g and brown in colour/3. The lock of hair underwent three consecutive cycles of thermal stress, as stated in the test procedure. At the end of each heat cycle, the hairs were collected and studied under a microscope at 100× oil immersion magnification The hair was treated with a leave-on formulation, formulated using polyglycerol-azelaic acid polyesters.

Results

Subjecting strands of hair to prolonged heat cycles, using a commercial hair straightener (GA.MA Italy, Professional Line, Mod. ART. 100) resulted in significant degradation and disorganisation of the cuticles of the hair subjected to thermal stress. This stress is demonstrated in FIG. 4B which shows a fragment of hair which underwent washing with a placebo formulation.

FIG. 5A shows how treating locks of hair from a single donor with a shampoo formulation containing polyglyceryl-3-azelaiate (1% w/v) with subsequent exposure of the locks to 3 consecutive heat cycles can decrease the thermal stress on the hair. Thermally stressed hair which has undergone washing with the formulation containing the active compound prior to each heat cycle acquires a protective film. Under microscopic observation, the hair treated in this way displays fewer cuticles, as they are presumably covered and protected by the protective film which is created.

FIG. 5B demonstrates treating locks of hair which have been treated with the leave-on formulation containing polyglyceryl-3-azelaiate (2% w/v), applied to wet locks after washing with a placebo shampoo formulation and followed by thermal stress. In particular, analysing the images shows that the leave-on formulation is able to create a protective layer on the hair which can protect the hair cuticles from applied thermal stress. This protective layer is clear and homogeneous at the end of stress.

In general, the results obtained have demonstrated the protective effect exerted by the two formulations, in the form of shampoo and leave-on lotion containing polyglyceryl-3-azelaiate, on hair subsequently subjected to repeated heat cycles which under normal conditions (application of a placebo shampoo formulation and repeated thermal stress) cause significant damage to the hair which manifests as deterioration and disorganisation of the hair cuticles.

What is claimed is:

1. A polyglycerol-azelaic acid polyester consisting of at least one unit of azelaic acid and at least one unit of polyglycerol, wherein the polyglycerol has 3 units of glycerol and a degree of polymerization of from 1.5 to 10.

2. The polyglycerol-azelaic acid polyester of claim 1 wherein the polyester is of the formula:

wherein n is from 1 to 7.

3. The polyglycerol-azelaic add polyester according to claim 1, having Mn in the range from 500 to 30,000 Daltons wherein the Mn is expressed in equivalent polystyrenes in size exclusion chromatography.

4. The polyglycerol-azelaic acid polyester according to claim 3, having Mn in the range from 1500 to 20,000 Daltons.

5. A polyglycerol-azelaic acid polyester consisting of at least one unit of azelaic acid and at least one unit of polyglycerol obtained by condensing azelaic acid with polyglycerol, wherein the polyglycerol has 3 units of glycerol and a degree of polymerization in the range from 1.5 to 10.

6. A cosmetic composition comprising a polyglycerol-azelaic acid polyester according to claim 1 and a cosmetically acceptable carrier.

7. The cosmetic composition according to claim 6, wherein the polyglycerol-azelaic acid polyester is obtained by reacting azelaic acid and polyglycerol-3, wherein the three glycerol units are connected with α-α bonds, represented below and wherein n is variable from 1 to 7.

8. A method for producing a polyglycerol-azelaic acid polyester consisting of at least one unit of azelaic acid and at least one unit of polyglycerol, said method comprising condensing azelaic acid with a polyglycerol having 3 units of glycerol and a degree of polymerization of from 1.5 to 10.

9. The method according to claim 8, wherein said polyglycerol is of the formula:

10. The method according to claim 8, wherein the condensation is carried out in the presence of an acid or a base.

11. The method according to claim 10, wherein said acid is para-toluenesulfonic acid.

12. The method according to claim 10, wherein the condensation is carried out in an inert atmosphere.

13. The method according to claim 12, wherein the condensation is carried out at a temperature of from 130° C. to 220° C.

14. A method for treatment of skin inflammation conditions, said method comprising applying a polyglycerol-azelaic acid polyester according to claim 1 to said skin.

15. The method according to claim 14, wherein the skin inflammation condition is acne.

16. A method for the cosmetic treatment of skin, said method comprising applying a polyglycerol-azelaic acid polyester according to claim 1 to said skin.

17. A method for protecting skin, skin appendages or hair from heat or from thermal treatments, said method comprising applying a polyglycerol-azelaic acid polyester according to claim 1 to said skin, said skin appendages or said hair.

18. A method for the cosmetic treatment of skin, said method comprising applying said cosmetic composition of claim 6 to said skin.

19. A method for protecting skin, skin appendages or hair from heat or from thermal treatments, said method comprising applying said cosmetic composition of claim 6 to said skin, said skin appendages or said hair.

* * * * *